(12) United States Patent
Kaplitt et al.

(10) Patent No.: US 8,182,460 B2
(45) Date of Patent: May 22, 2012

(54) INFUSION DEVICE AND METHOD FOR INFUSING MATERIAL INTO THE BRAIN OF A PATIENT

(75) Inventors: Michael G. Kaplitt, New York, NY (US); Matthew J. During, New York, NY (US)

(73) Assignee: Medtronic, Inc., Minneapolis, MN (US)

( * ) Notice: Subject to any disclaimer, the term of this patent is extended or adjusted under 35 U.S.C. 154(b) by 73 days.

(21) Appl. No.: 12/702,470

(22) Filed: Feb. 9, 2010

(65) Prior Publication Data
US 2010/0191218 A1 Jul. 29, 2010

Related U.S. Application Data

(62) Division of application No. 11/280,965, filed on Nov. 16, 2005, now abandoned.

(60) Provisional application No. 60/629,759, filed on Nov. 19, 2004.

(51) Int. Cl.
*A61M 31/00* (2006.01)

(52) U.S. Cl. .................................................. 604/500

(58) Field of Classification Search .................. 604/117, 604/103.07, 103.1, 264, 513, 43, 157, 173, 604/164.02, 164.01; 606/108
See application file for complete search history.

(56) References Cited

U.S. PATENT DOCUMENTS

| | | | |
|---|---|---|---|
| 4,737,146 A | 4/1988 | Amaki | |
| 5,085,631 A | 2/1992 | Leighton | |
| 5,697,975 A * | 12/1997 | Howard et al. | 623/10 |
| 5,782,798 A | 7/1998 | Rise | |
| 5,792,110 A | 8/1998 | Cunningham | |
| 6,093,180 A | 7/2000 | Eisberry | |
| 6,272,370 B1 * | 8/2001 | Gillies et al. | 600/411 |
| 6,295,990 B1 | 10/2001 | Lewis | |
| 6,893,421 B1 | 5/2005 | Larson | |
| 7,008,412 B2 | 3/2006 | Maginot | |

(Continued)

FOREIGN PATENT DOCUMENTS

WO   WO 03/005908   1/2003

(Continued)

OTHER PUBLICATIONS

PCT International Search Report dated Jan. 2, 2008.

(Continued)

*Primary Examiner* — Christopher D Koharski
(74) *Attorney, Agent, or Firm* — Mueting, Raasch & Gebhardt, P.A.

(57) ABSTRACT

A fluid infusion device and a method of using the same. The device includes an outer, flexible guide catheter having a distal end for introduction beneath the skull of a patient and a proximal end remaining external of the patient. A flexible infusion fiber is located within the guide catheter and has a distal end extending outwardly from the guide catheter to be located in a target area within the patient's brain. The infusion fiber can be fixed or axially movable within the guide catheter. In the latter embodiment, the proximal end of the infusion fiber extending outwardly from the guide catheter can be manipulated to locate the distal end of the infusion fiber in the target area. An infusion pump is connected to the proximal end of the infusion fiber to infuse a minute quantity of fluid at an extremely low flow rate into the brain of the patient.

16 Claims, 3 Drawing Sheets

U.S. PATENT DOCUMENTS

| | | |
|---|---|---|
| 7,077,822 B1 | 7/2006 | Howard |
| 2001/0047196 A1 | 11/2001 | Ginsburg |
| 2003/0032942 A1 | 2/2003 | Theeuwes |
| 2003/0036726 A1 | 2/2003 | Forman |
| 2003/0167031 A1 | 9/2003 | Odland |
| 2004/0049121 A1 | 3/2004 | Yaron |
| 2004/0064086 A1 | 4/2004 | Gottlieb |
| 2004/0181206 A1 | 9/2004 | Chiu |
| 2004/0215162 A1 * | 10/2004 | Putz .............................. 604/500 |

FOREIGN PATENT DOCUMENTS

| | | |
|---|---|---|
| WO | WO 03/077785 | 9/2003 |

OTHER PUBLICATIONS

Supplemental EP Search Report dated Nov. 20, 2009.

* cited by examiner

INFUSION DEVICE AND METHOD FOR INFUSING MATERIAL INTO THE BRAIN OF A PATIENT

RELATED APPLICATION

This application is (i) a divisional application of U.S. patent application Ser. No. 11/280,965, filed on Nov. 16, 2005, which application published as US 2006/0129126 on Jun. 15, 2006, and (ii) claims the benefit of priority to U.S. Provisional Patent Application Ser. No. 60/629,759, filed Nov. 19, 2004 and entitled "INFUSION DEVICE AND METHOD FOR INFUSING MATERIAL INTO THE BRAIN OF A PATIENT".

BACKGROUND

The present invention relates to infusion devices for introducing fluids into a patient and, more particularly, to an infusion device and method of infusing minute volumes of liquid at extremely low flows into the brain of a patient.

There are certain procedures carried out on a patient where extremely minute, sub-milliliter amounts of fluids or suspensions are directly infused into the brain of the patient and such fluids can include therapeutic drugs or biological material including peptides, proteins, viral vectors, DNA, RNA and other nucleic acids, lipids and liposomes, polymers, dendrimers and the like or combinations thereof The fluids are infused into a particular target area within the brain that may range from about 1 mm$^3$ to as large as several cubic centimeters. In any event it is extremely important to accurately reach the target area with the particular fluid and to infuse the fluid into the patient at that desired location, adequately covering the desired area in a controlled fashion.

Since the actual infusion is of minute quantities of fluid and with flow rates of the infused fluid very slow, i.e. several nanoliters to up to 1 ml or more infused at a rate of, for example, 1.0 nl/min to several microliters/min, the infusion device must be very minute and must be accurately placed at or proximate to the target area. Additionally, since the infusion device is actually located within the brain, it is desirable that the end of the device that is infusing the fluid be somewhat flexible and preferably move with the brain during respiration since a rigid device can cause trauma to the brain tissue and/or brain hemorrhage. This is particularly true since the infusion device may be implanted to remain over a substantial period of time extending at least several hours to days or more. It is also desirable to have a device which is sufficiently resilient that it can be secured with a fixation device to prevent movement away from the target without damaging the catheter infusion system. It is also desirable to have a system which can be imaged to confirm the location in the brain and to ensure that the catheter has not moved from the target at any point.

Accordingly, one current method of infusing such fluids is to utilize a radioopaque catheter having an internal diameter of about 1.3 mm. into the brain and attach an infusion pump to the catheter. The catheter is normally introduced by means of a relatively rigid stylet that is inserted into the brain to the target area and the catheter then threaded over the stylet with the stylet being removed after the distal end of the catheter is located at the target area. Such catheter has, however, a rather large dead space due to the very dimensions of that catheter. This large dead space limits reliability and reproducibility of infusions, particularly for small volumes of fluid, due to the large errors and insensible losses inherent in catheters with dead spaces which are significantly greater that the actual volume of fluid to be infused. In addition, large catheters cause significant damage to the brain in the area of infusion. This not only can confound therapeutic results, it can also limit the effectiveness and reliability of the infusion. For example, larger catheters in animal subjects have been found to result in more limited diffusion in the brain compared with smaller catheters. This likely is due to the fact that damage from a larger catheter causes fluid to pool in the cavity caused by the damage, while infusing through intact brain via a smaller catheter causes the fluid to diffuse more reliably in the natural interstitial space of normal tissues.

This creates a dilemma, however. Although fine catheters are desirable, very fine systems do not usually have the resiliency or strength to withstand long term use. This would be particularly true for catheters which would be externalized and attached to an infusion pump, since these would be particularly subject to damage by the patient or by routine healthcare workers. Clamping very fine catheters in fixation devices, usually requiring catheters to be bent at extreme angles, would also likely break or obstruct a fine catheter. Similarly, an extremely fine catheter is difficult to visualize by imaging, even when impregnated with a contrast agent, due to resolution limits of current imaging systems.

Therefore, there is a need for a catheter system which has a sufficiently small diameter at the distal, infusion end to minimize local tissue trauma, with a very small dead space yet with the strength of a larger catheter to prevent breakage and permit fixation, and with the ability to visualize the catheter by imaging. A system harboring all of these features currently does not exist. Current systems for infusion are largely designed for infusion into fluid channels, such as intravascular or intrathecal infusion, and thus are limited in one of more of the criteria outlined above. What is described in this application is a novel concept for an infusion system which incorporates all of these features which are key to optimizing infusion of small volumes of fluid directly into solid tissue targets.

SUMMARY OF THE INVENTION

Accordingly, the present invention relates to an infusion device that can be utilized effectively and accurately to infuse a minute quantity of a liquid at an extremely low flow rate into a desired target area of the brain of a patient.

In the infusion device of the present invention, the device comprises an outer, flexible guide catheter that has a distal end and a proximal end and at least one lumen therethrough. As will be later described, the guide catheter may have a plurality of lumens (as well as a possible lumen running parallel to the external wall of the device). The distal end of the flexible guide catheter is adapted to be introduced through the skull of the patient to enter the brain so as to be located at a desired area within the brain. The guide catheter may be partially or entirely radioopaque in order for the physician to properly locate the distal end of the guide catheter at the desired location within the brain of the patient. Alternatively, or additionally, there may be other means of ascertaining the location of the distal end of the guide catheter, including, but not limited to, the impregnation of the catheter with a material to render the catheter visible through CT or MRI techniques. Other means of determining the location of the guide catheter can be employed such as a miniaturized or nanotechnology, GPS receiver, it only being of importance that the user be able to clearly ascertain the location within the patient of the distal end of the catheter. The guide catheter may be constructed of a variety of flexible materials common for medical catheters such as polyethylene, silastic or other plastic or composite materials.

The proximal end of the flexible guide catheter remains external of the skull and scalp of the patient when the present fluid infusion device is properly located and ready to be used and that guide catheter may be sutured, or otherwise fixed, to the scalp in order to retain it in the usable position while the liquid is being infused. Alternatively, the proximal end is external to the skull but remains in a subgaleal position attached to a small, subgaleal infusion pump. The proximal portion may also reside within the burr hole, attached to a reservoir or small infusion pump designed to rest within the burr hole.

A hollow, flexible infusion fiber is positioned within the lumen of the single lumen guide catheter, or within one of the lumens in the event a multi-lumen guide catheter is utilized. The flexible infusion fiber also has a distal end and a proximal end. The infusion fiber is dimensioned to be snugly fitted within and axially movable or fixed in position within the guide catheter and has its proximal end extending outwardly from the proximal end of the guide catheter and with the distal end of the infusion fiber extending outwardly from the distal end of the guide catheter. When the infusion fiber is fixed and immoveable within the guide catheter, the distal end is located a fixed distance from the distal end of the guide catheter. If axially movable within the guide catheter, the distal end of the infusion fiber can be extended outwardly to the desired location a distance from the distal end of the guide catheter. In either event, the infusion fiber is of a lesser diameter than the guide catheter so that the tissue to be infused need not be entered by the larger guide catheter, minimizing tissue trauma.

As such, where the infusion fiber is axially movable within the guide catheter, the user can manipulate the proximal end of the infusion fiber to extend or retract the distal end of the infusion fiber with respect to the distal end of the guide catheter, that is, in the placement of the present infusion device, the user can move the distal end of the infusion fiber outwardly or inwardly from the distal end of the guide catheter. Where the infusion fiber is fixed within the guide catheter, the distal end of the infusion fiber extends a fixed distance from the distal end of the guide catheter without movement. In either case, the exposed distance of the infusion fiber beyond the distal end of the catheter may be between about 0.5 mm. to about 50 mm. or more in order to locate the distal end of the infusion fiber at the desired target area within the brain of the patient. In a preferred embodiment, the exposed distance of the infusion fiber is from about 1 to about 20 mm.

Accordingly, the infusion device can allow the flexible infusion fiber to enter the brain, particularly deep brain structures, and the critical component, the flexible end of the infusion fiber that extends the desired distance outwardly from the distal end of the guide catheter, can be movable within the brain to float therein. The distal end of the infusion fiber, therefore, is a very fine component that extends outwardly from the larger guide catheter component at a distance determined by the physician placing the infusion device.

Due to the particular dimensions of the infusion fiber, there is very little dead space and the extremely small size minimizes the possibility that the infused fluid tracks back along the infusion fiber track, that is, the infusion of fluid is restricted to the particular target area which, as explained, can be as small as 1 mm$^3$, or as large as several cubic centimeters. The larger guide catheter, whether or not the infusion fiber is fixed, provides stability and strength (protecting the fragile inner infusion fiber) as well as imaging capabilities, but only enters the tissue proximal to the target and thus does not significantly damage the target tissue.

Of importance, also, is that the infusion device, once in place, need not be stabilized by attachment to the skull itself or a stereotactic frame, since it is designed to float in the brain. The stabilization of the infusion device can, therefore, simply be carried out by the aforedescribed suturing, or other means of affixing, the guide catheter to the scalp. That floating effect also avoids the microtrauma and/or hemorrhage associated with the more rigid devices and the floating effect allows the distal end of the infusion fiber to move in relationship to the brain during physiological movement associated with coughing, sneezing, respiration, physical activity or the like. Nonetheless, the more substantial proximal guide catheter protects the fragile inner infusion fiber, permitting fixation to the skull and/or scalp to prevent withdrawal of the catheter from the target, which can be a problem common to current infusion systems which were never designed for infusion into solid tissue such as the brain. Potential fixation methods include, but are not limited to, fixation to the skull near the burr hole with a metal plate, such as a titanium plate, fixation with a plastic capping system placed within the burr hole, or externalization through the scalp and suturing of the guide catheter to the scalp.

In one specific embodiment, a new fixation device is described. This device involves securing a base cap to the burr hole. A winged clamp is then secured to the guide catheter, grabbing and securing the guide catheter via a removable tightener which tightens the clamp to the point of grabbing the guide catheter while not obstructing or damaging the inner infusion fiber. The wings of the clamp are then secured to the base cap, either via small screws or via a plastic locking system. A third stage may or may not be placed to cover the base and clamp.

The flexible infusion fiber can be constructed of a variety of materials, among which are vitreous silica, fused silica, silastic polyurethane or other plastic material as well as metal or composite materials providing there is a certain flexibility of the infusion fiber. As stated, the dimensions of the infusion fiber are extremely minute and, in one embodiment, range from about 100 microns inner diameter plus or minus about 10 microns with a outer diameter of about 170 microns, again with a tolerance of plus or minus about 10 microns.

The proximal end of the infusion fiber can also have a connector means to allow the infusion fiber to be fluidly connected to a pump to introduce the fluid into and through the infusion fiber. That infusion pump may be simply a syringe or can be an automatic system such as a syringe pump or miniaturized microinfusion pump to introduce the fluid at extremely low flow rates and minute quantities of fluid to be administered to the brain of the patient.

For example typical flows are in the range of about 1 nl/min to about 5.0 microliters/min. A preferred embodiment is 10 nl/min. to about 1 microliter/min and, in a more preferred embodiment, flow rates are 100 nl/min to about 0.5 microliters/min. Total quantities of fluid to be infused may typically range between about 1 microliter to 5 milliliters, with a preferred embodiment being 5 microliters to 1 milliliter and a more preferred embodiment being 10 microliters to 500 microliters. However, other flow rates and quantities of fluid may vary depending upon the particular fluid and dosage being administered.

In an alternate embodiment, the guide catheter may be a multilumen catheter where, in addition to the infusion lumen, other lumens may be available for the use of additional infusion fibers, stylets, miniaturized biopsy needles, electrodes, biosensors, temperature monitors, optical fibers and the like. For example, a fine microelectrode can be threaded through a lumen of the guide catheter in order to enable single cell recordings. The individual lumens of the multilumen catheter may, of course, be of a uniform inner diameter or the diameters varied in accordance with the particular use of the lumens. Similarly, an optical fiber can be threaded through a lumen to detect a light-emitting compound such as luciferin within the infusate to monitor infusion parameters. A thermal probe could similarly be threaded through a lumen to monitor infusion parameters as a reflection of tissue thermodilution as a room temperature fluid is infused into the warm brain.

Additional features and advantages of the invention will become apparent to those skilled in the art upon consideration of the following detailed description of preferred embodiments exemplifying the best mode of carrying out the invention.

DETAILED DESCRIPTION OF THE INVENTION

Figure 1:
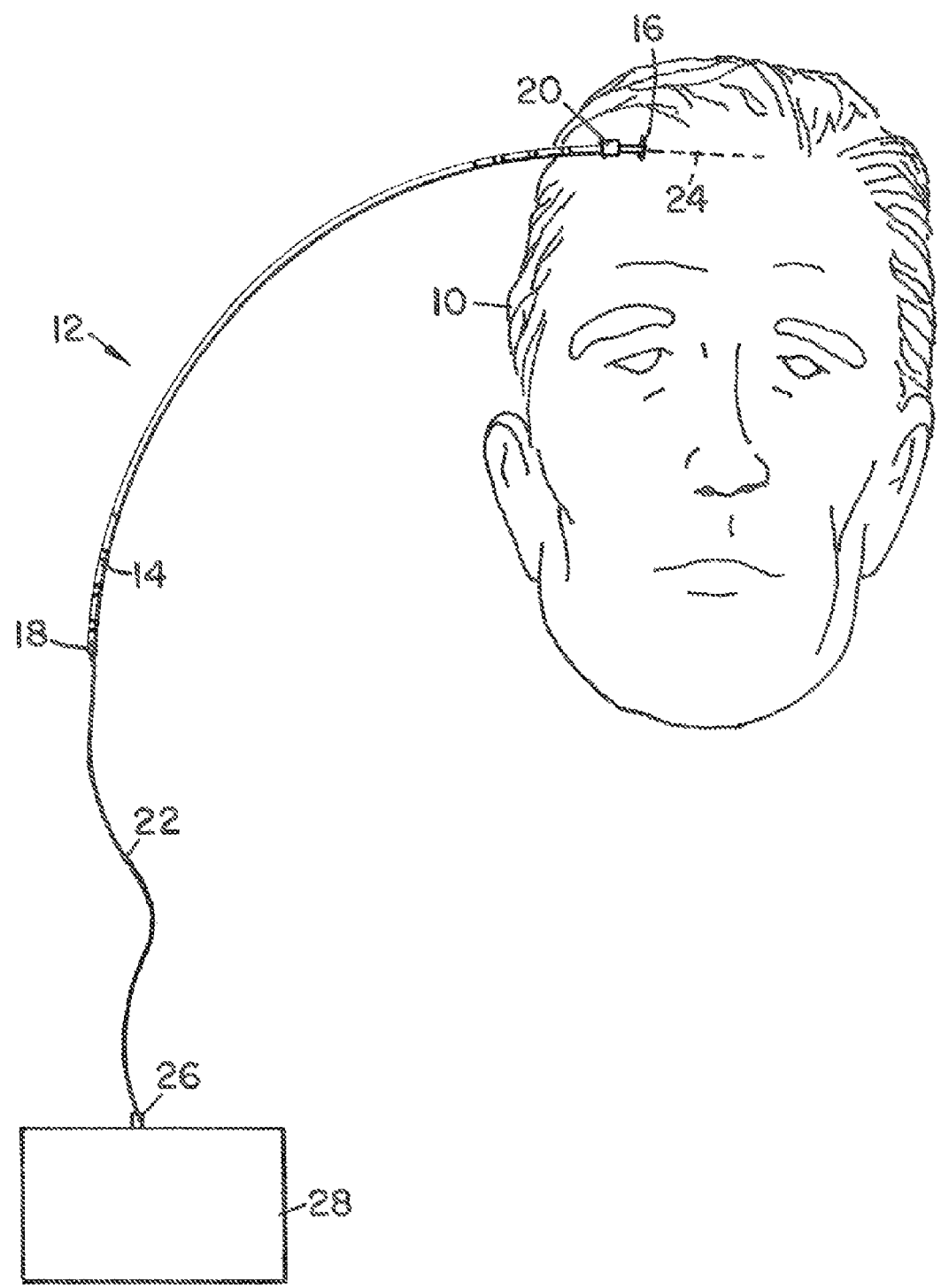
FIG. 1 is a view of the skull of a patient illustrating the positioning of the fluid infusion device of the present invention.

Referring now to FIG. 1, there is shown a front view of the skull 10 of a patient illustrating the operative position of an infusion device 12 constructed in accordance with the present invention. As can be seen, there is a flexible guide catheter 14 that has a distal end 16 and a proximal end 18. In the use of the infusion device 12, as will be later explained, the distal end 16 is preferably located within the interior of the skull 10 of the patient whereas the proximal end 18 can be normally located exterior of the patient, or also remain under the scalp.

Once positioned as shown in FIG. 1, the guide catheter 14 can be affixed to the scalp of the patient by means of one or more sutures 20 or by other methods. The actual location of the distal end 16 of the guide catheter 14 can be achieved through the use of a stereotactic frame, by frameless means or even manually.

The infusion device 12 also includes a flexible infusion fiber 22 that is threaded within a lumen of the guide catheter 14 so as to move axially therein in a snug fit or be immovable therein. The infusion fiber 22 has a distal end 24 and a proximal end 26 and again, in the operative position, the distal end 24 is located within the brain of the patient situated at a particular target area where the infusion of fluid is desired to take place and the proximal end 26 is located external of the patient. In the embodiment shown, the proximal end 26 is fluidly connected to a fluid pump 28 which may be simply a syringe containing the particular fluid to be infused or may be some automated pumping device such as a syringe pump or miniaturized microinfusion pump that infuses fluid into the proximal end 26 of the infusion fiber 22 at a predetermined rate. Thus, it is possible to have the infusion fiber 22 directly attached to a pump or reservoir which resides either under the scalp of the patient or within the burr hole as part of a completely internalized system.

As stated, the hollow, flexible infusion fiber 22 may be constructed of various materials, among which are both vitreous silica, fused silica, silastic or polyurethane or other plastic hollow fibers as well as metals or composite materials.

Figure 2:
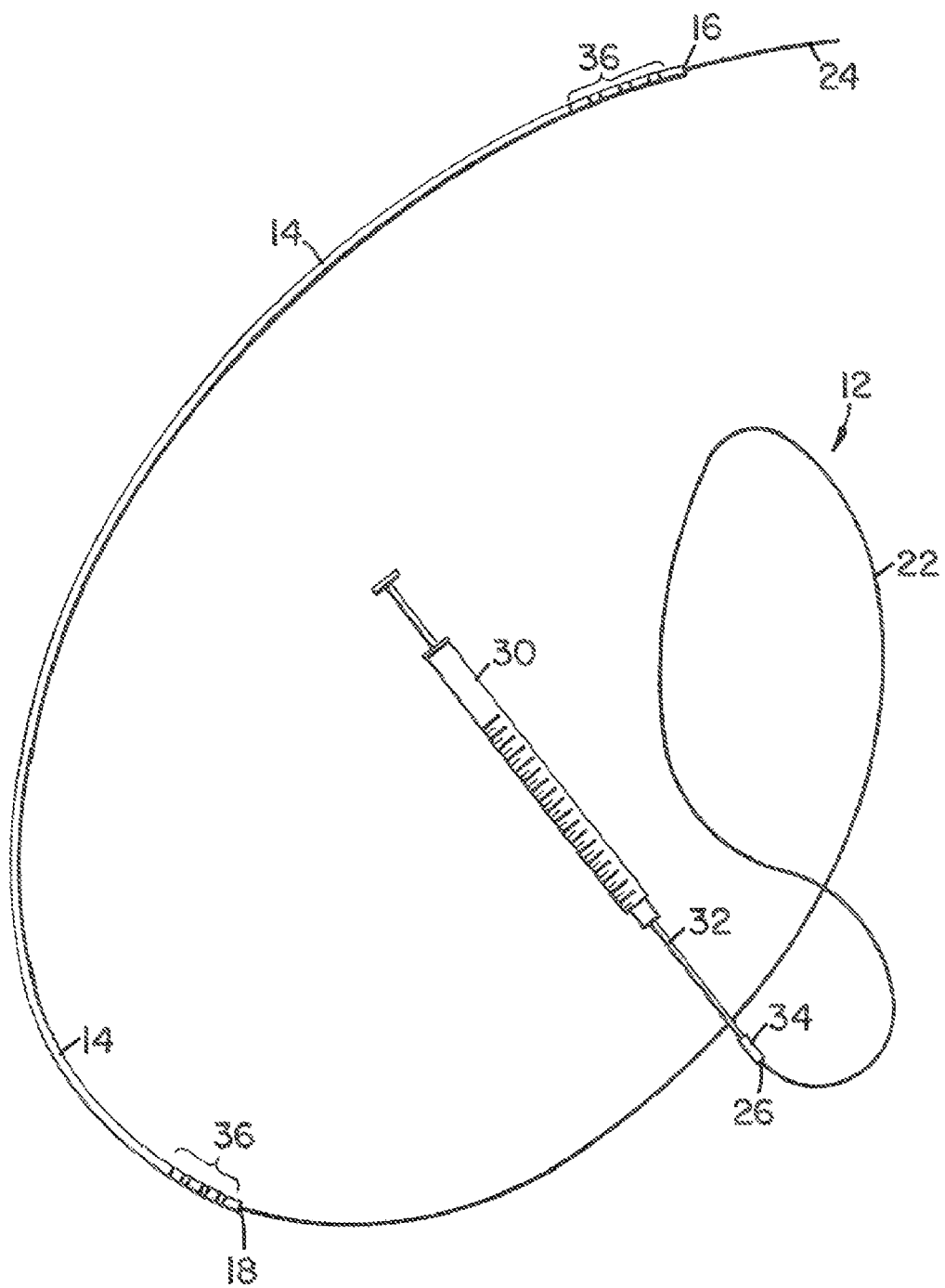
FIG. 2 is a perspective view of the fluid infusion device of the present invention.

Turning now to FIG. 2, there is a perspective view of an infusion device 12 of the present invention showing a syringe 30 affixed thereto to in order to introduce fluid into the proximal end 26 of the flexible infusion fiber 22. Accordingly, the syringe needle 32 extending outwardly can be connected to the proximal end 26 of the infusion fiber 22 by means such as a plastic sleeve 34 that can be affixed to the proximal end 26 of the infusion fiber 22 by an adhesive and which slips over the syringe needle 32 to allow the fluid within the syringe 30 to be introduced into the infusion fiber 22 at a controlled, known rate. The plastic sleeve 34 can be constructed of a clear plastic such as polyurethane, however, the connection by the use of a plastic sleeve 34 is illustrative only and there are many suitable ways of connecting the proximal end 26 of the infusion fiber 22 to the syringe 30 or to an infusion pump.

As an example of the use of the present infusion device 12, a viral vector can be delivered at a rate of 0.5 microliters per minute to infuse 50 microliters of the material and takes 100 minutes to carry out that infusion. Larger volumes and more rapid delivery flow rates may be used, however, for epilepsy cases, for example, where the quantity may be in the order of 200 microliters and may take up to several hours to administer the fluid. For some applications, slower infusion rates as low as a nanoliter a minute can be used and carried out over days of infusion.

The guide catheter may also include a plurality of metal bands 36 located at the distal end 16 and the proximal end 18 and which are used as electrodes enabling field potentials to be recorded or for tissue to be transiently electrically simulated for either diagnostic localization purposes or to modulate infusion dynamics.

As shown in FIG. 2, taken along with FIG. 1, the distal end of the infusion fiber 22 extents about 20 mm. outwardly from the distal end 16 of the guide catheter 14, however, in the embodiment, the distal end of the infusion fiber 22 can be extended from about 0.5 mm to about 50 mm from the distal end 16 of the guide catheter 14.

The method of introducing the infusion fiber 22 into the target area within the brain of a patient can now be explained. The guide catheter 14 can be inserted though the skull 10 and into or proximate to the brain of the patient. That introduction may be through the use of a stereotactic frame, a frameless stereotaxy procedure or may even be carried out manually (free hand) by the physician. The guide catheter may be inserted through a removable, rigid outer guide tube, or alternatively a rigid, removable stylet may be included in the wall of the guide catheter 14 for direct introduction into the brain. In either event, the rigid component is quickly removed after placement at target.

During insertion, the distal end 16 of the guide catheter 14 can be monitored by the use of the radioopaque techniques, CT, MRI or other means of accurately ascertaining and maintaining the location of the distal end 16. Once that distal end 16 has been located in the proper desired position, the guide catheter 14 can be sutured or otherwise affixed to the scalp of the patient to retain the guide catheter 14 in place or can be fixed to the skull by one of the means described above. In the embodiment where the infusion fiber 22 is axially movable within the guide catheter 14, the proximal end 26 of the infusion fiber 22 can be manipulated so as to extend outwardly the distal end 24 of the infusion fiber 22 from the distal end 16 of the guide catheter 14 so that the distal end 24 of the infusion fiber 22 becomes positioned at the target area within the brain where the fluid is desired to be introduced. In the embodiment where the infusion fiber 22 is fixed within the guide catheter 14, the distal end 16 of the infusion fiber 22 would already be extended a fixed distance upon entry of the entire system.

Figure 3:
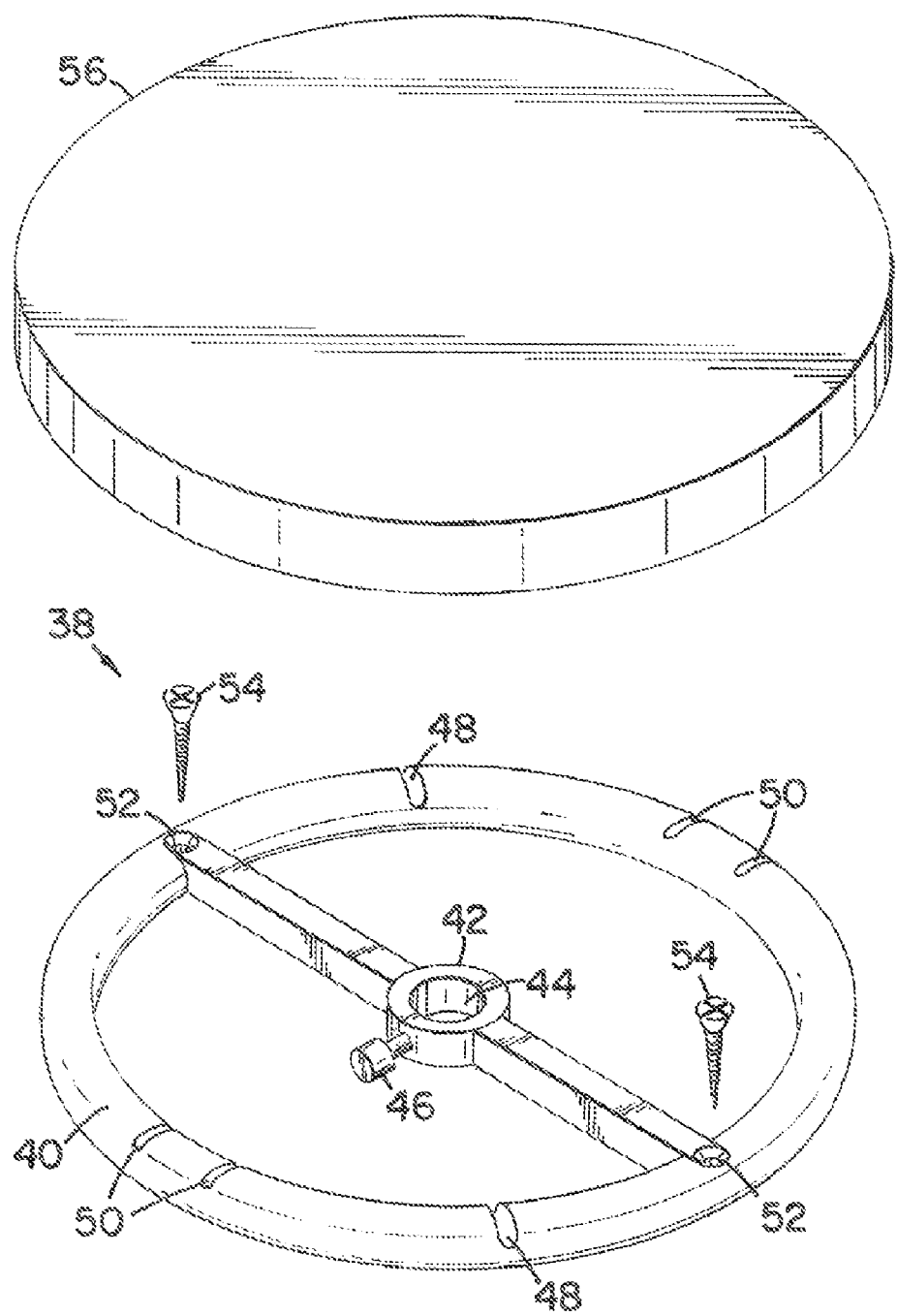
FIG. 3 is a partially exploded view of a fixation device that can be used to secure the fluid infusion device of the present invention to a patient.

Turning now to FIG. 3, taken along with FIGS. 1 and 2, there is shown a fixation device 38 that can be used in connection with the infusion device of the present invention to secure that infusion device 12 to the patient so that the distal end 16 of the guide catheter 14 as well as the distal end 24 of the infusion fiber 22 remains in the correct location within the brain of the patient to infuse the fluid to the target area. Accordingly, as can be seen in FIG. 3, the fixation device 38 comprises a base cap 40 that can be generally round or other configuration. The base cap 40 includes a ring 42 having an opening 44 formed therein and which is, in use, adapted to be aligned with the burr hole that is created in the patient's skull for introduction of the infusion device 12 into the patient.

The ring 42 also includes a tightener 46 that can be adjusted to secure and grab the guide catheter 14 securely to the base cap 40. In such manner, the guide catheter 14 can be threaded through the opening 44 and the tightener 46 used to secure the guide catheter 14 in a fixed location to the base cap 40. The tightener 46 can be a threaded screw, as shown, or may be other means, it being of importance that the tightening of the tightener 46 be carried out without occluding or damaging the infusion fiber 22 that is located within the guide catheter 14. The upper surface of the base cap 40 may also have one or more slits 48 that are indented into the material of the base cap 40 so that the guide catheter 14 can fit within a slit 48. As also can be seen, there may be one or more openings 50 formed in the upper surface of the base cap 40.

In addition there are one or more holes 52 that are formed passing through the base cap 40 to accommodate the introduction of screws 54 that are used to secure the base cap 40 to the patient. As such, with the base cap 40 securely affixed to the patient's skull, it can be seen that the guide catheter 14 itself is also securely affixed to the patient so as to maintain the integrity of the particular location of the distal end 16 of the guide catheter 14 as well as the distal end 24 of the infusion fiber 22.

There is also shown a cap 56 that can be snapped onto the base cap 40 to cover the base cap and the burr hole for protection thereof The cap 56 may have one or more protuberances that snap into the openings 50 to secure the cap 56 in place.

Those skilled in the art will readily recognize numerous adaptations and modifications which can be made to the present infusion device and method of use thereof which will result in an improved device and method yet all of which will fall within the scope and spirit of the present invention as defined in the following claims. Accordingly, the invention is to be limited only by the following claims and their equivalents.

We claim:

1. A method of infusing a fluid at a low flow rate into the brain of a patient, comprising:
    providing an outer, flexible guide catheter having a distal end, a proximal end and a lumen therethrough;
    providing a hollow, flexible infusion fiber having a distal end and a proximal end, said infusion fiber being located within the lumen of the guide catheter, said proximal end of the infusion fiber extending outwardly from the proximal end of the guide catheter, said infusion fiber having an inlet located at the proximal end of the infusion fiber for receiving fluid to pass fluid through the infusion fiber to the distal end of the infusion fiber positioned proximate to the brain of the patient, wherein the inner diameter of the flexible infusion fiber is between about 90 microns and about 110 microns;
    locating the flexible infusion fiber within the lumen of the guide catheter such that (i) the flexible infusion fiber is axially movable within the guide catheter, and (ii) the proximal end of the infusion fiber extends outwardly from the proximal end of the guide catheter and the distal end of the infusion fiber extends outwardly from the distal end of the guide catheter,
    locating the guide catheter at a predetermined location within the brain of a patient,
    securing the guide catheter to the scalp of a patient;
    introducing fluid into the proximal end of the infusion fiber to cause fluid to pass from the distal end of the infusion fiber at the desired location within the brain of a patient,
    wherein the guide catheter and the infusion fiber are sufficiently flexible such that when the guide catheter is affixed to the scalp of the patient but not to the skull of the patient, the guide catheter and infusion fiber are capable of moving in the brain of the patient without causing hemorrhage.

2. The method of claim 1, wherein locating the flexible infusion fiber within the lumen of the guide catheter comprises locating the flexible infusion fiber to be axially movable within the guide catheter.

3. The method of claim 1, further comprising extending the infusion fiber outwardly from the distal end of the guide catheter to locate the distal end of the infusion catheter at a desired location within the brain of a patient.

4. The method of claim 1, further comprising extending the infusion fiber outwardly from the distal end of the guide catheter to locate the distal end of the infusion catheter at a desired location within the brain of a patient.

5. The method of claim 1, wherein introducing the fluid into the proximal end of the infusion fiber comprises introducing a liquid at the rate of about 1.0 nl/min to 5.0 microliters/min.

6. The method of claim 1, wherein securing the outer guide catheter to the scalp of a patient comprises suturing the guide catheter to the scalp of a patient.

7. The method of claim 1, wherein the step of extending the infusion fiber outwardly from the distal end of the guide catheter comprises extending the distal end of the infusion fiber from about 0.5 mm to about 50 mm from the distal end of the guide catheter.

8. The method of claim 1, wherein providing a guide catheter comprises providing a guide catheter having a marking material to enable the position of the guide catheter to be determined.

9. The method of claim 2, wherein the guide catheter is not secured to the skull of the patient.

10. The method of claim 3, wherein the guide catheter is not secured to the skull of the patient.

11. The method of claim 1, wherein the guide catheter is not secured to the skull of the patient.

12. The method of claim 4, wherein the guide catheter is not secured to the skull of the patient.

13. The method of claim 5, wherein the guide catheter is not secured to the skull of the patient.

14. The method of claim 6, wherein the guide catheter is not secured to the skull of the patient.

15. The method of claim 7, wherein the guide catheter is not secured to the skull of the patient.

16. The method of claim 8, wherein the guide catheter is not secured to the skull of the patient.

* * * * *